(12) United States Patent
Guida et al.

(10) Patent No.: US 6,929,912 B2
(45) Date of Patent: Aug. 16, 2005

(54) METHODS FOR EVALUATING THE ABILITY TO METABOLIZE PHARMACEUTICALS

(75) Inventors: Marco Guida, San Diego, CA (US); Jeff Hall, Carlsbad, CA (US); William P. Petros, Morgantown, WV (US); James J. Vredenburgh, Chapel Hill, NC (US); Oliver M. Colvin, Chapel Hill, NC (US); Jeffrey R. Marks, Hillsborough, NC (US)

(73) Assignees: Genaissance Pharmaceuticals, Inc., New Haven, CT (US); Duke University, Durham, NC (US)

(*) Notice: Subject to any disclaimer, the term of this patent is extended or adjusted under 35 U.S.C. 154(b) by 0 days.

(21) Appl. No.: 10/085,612

(22) Filed: Feb. 26, 2002

(65) Prior Publication Data

US 2003/0096251 A1 May 22, 2003

(Under 37 CFR 1.47)

Related U.S. Application Data

(63) Continuation-in-part of application No. 09/144,367, filed on Aug. 31, 1998, now Pat. No. 6,432,639.
(60) Provisional application No. 60/271,630, filed on Feb. 26, 2001.

(51) Int. Cl.[7] .......................... C12Q 1/34; C12Q 1/44; C12P 19/34; C07H 21/04
(52) U.S. Cl. .......................... 435/6; 435/19; 435/91.2; 536/23.2; 536/23.5; 536/24.31; 536/24.33
(58) Field of Search .......................... 435/6, 19, 91.2; 536/23.2, 23.5, 24.31, 24.33

(56) References Cited

U.S. PATENT DOCUMENTS

| | | | |
|---|---|---|---|
| 5,413,915 A | 5/1995 | Case et al. ..................... | 435/25 |
| 5,420,027 A | 5/1995 | Fisher et al. ................ | 435/189 |
| 5,445,934 A | 8/1995 | Fodor et al. ................... | 435/6 |
| 5,478,723 A | 12/1995 | Parkinson et al. ............. | 435/4 |
| 5,506,131 A | 4/1996 | Harris et al. ............. | 435/240.2 |
| 5,660,986 A | 8/1997 | Harris et al. .................... | 435/6 |
| 6,174,684 B1 * | 1/2001 | Rebbeck et al. ............... | 435/6 |
| 6,183,963 B1 | 2/2001 | Sinnett et al. ................ | 435/6 |

FOREIGN PATENT DOCUMENTS

| | | |
|---|---|---|
| WO | 92/19647 | 11/1992 |
| WO | WO 93/18178 | 9/1993 |
| WO | 95/35505 | 12/1995 |
| WO | WO 99/13106 | 3/1999 |
| WO | WO 00/39332 | 7/2000 |

OTHER PUBLICATIONS

Petros, W. et al. Associations between variants in several drug metabolism genes and chemotherapy pharmacokinetics or clinical response. Proceedings of the American Association for Cancer Research Annual Meeting 42:266 (Mar. 2001).*

Van Schaik, R. et al. CYP3A4–V polymorphism detection by PCR–restriction fragment length polymorphism analysis and its allelic frequency among 199 Dutch caucasians. Clinical Chemistry 46(11):1834–1836 (2000).*

Ambrosone, C. et al. Polymorphisms in glutathione S–transferases (GSTM–1 and GGTT1) and survival after treatment for breast cancer. Cancer Research 61:7130–7135 (Oct. 2001).*

Felix et al., "Association of CYP3A4 genotype with treatment–related leukemia"; *Proc. Natl. Acad. Sci. USA;* vol. 95, 1998, pps. 13176–81.

Howells et al., "Association of Glutathione S–Transferase GSTM1 and GSTT1 Null Genotypes with Clinical Outcome in Epithelial Ovarian Cancer"; *Clinical Cancer Research;* vol. 4; 1998, pps. 2439–45.

Jungnellus, et al., "Simliar Toxic Effect of 1,3–BIS(2–Chloroethyl–1–Nitrosourea on Lymphocytes from Human Subjects Differing in the Expression of Glutathione Transferase M1–1"; *Biochemical Pharmacology;* vol. 47:10; 1994, pps. 1777–80.

Klrchea et al., "MGMT–and P450 3A–inhibitors do not sensitize glioblastoma cell cultures against nitrosoureas"; *Clinical Neuropathology;* vol. 18:1; 1999, pps. 1–8.

Lizard–Nacol et al., "Glutathione S–transferase M1 null genotype: lack of association with tumour characteristics and survival in advanced breast cancer"; *Breast Cancer Res.;* vol. 1:1; 1999, pps. 81–87.

Nakamura et al., "Apparent Low Frequency of Sequence Variability within the Proximal Promoter Region of the Cytochrome P450 (CYP) 3A5 Gene in Established Cell Lines from Japanese Individuals"; *Biol. Pharm. Bull.;* vol. 24:8; 2001, pps. 954–57.

Brian et al., *Biochemistry,* 29: 11280–11292 (1990).

Carter et al., *Biochem.,* 197(2):301–308 (1995).

Delahunty et al., *Am. J. Hum. Genet.,* 58: 1239–1246 (1996).

DeRisi et al., *Nature Genetics,* 14: 457–460 (1996).

Golovieve et al., *Am. J. Hum. Genet.,* 59: 570–579 (1996).

Gonzalez et al., GenBank Accession No. M18907, Jun. 1989.

(Continued)

*Primary Examiner*—Diana B. Johannsen
(74) *Attorney, Agent, or Firm*—Melodie Henderson; Sandra Shaner; Robert Trauer

(57) ABSTRACT

Methods for detecting variant genes having a polymorphism associated with reduced metabolism of a substrate selected from the group consisting of a CYP3A4 substrate, a CYP3A5 substrate and a GSTM1 substrate in an individual are disclosed. The methods are genotyping methods to identify specific polymorphisms which have been found to be associated with reduced metabolism of chemotherapeutic agents, such as cyclophosphamide and BCNU. Also disclosed are novel polymorphic nucleic acid molecules useful in the methods of the invention.

15 Claims, No Drawings

OTHER PUBLICATIONS

Hacia et al., *Nature Genetics*, 14: 441–447 (1996).
Hashimoto et al., *Eur. J. Biochem.*, 218: 585–595 (1993).
Hashimoto et al., GenBank Accession No. D11131, Jan. 1994.
Hiller et al., GenBank Accession No. H21215 (1995).
Jounaidi et al., GenBank Accession No. S74700, Apr. 1995.
Kawagish, GenBank Accession No. X59297 (1991).
Lewis et al., *Toxicology*, 125: 31–44 (1998).
Lockhart et al., *Nature Biotechnology*, 14: 1675–1680 (1996).
Lown et al., *J. Clin. Invest. The American Society for Clinical Investigation, Inc.*, 99(10): 2545–2553 (1997).
Mansfield et al., *Genomics*, 24: 225–233 (1994).
Marra, et al., GenBank Accession No. W35854 (1996).
Saiki et al., *Science*, 239: 441–532 (1988).
Sambrook et al., Molecular Cloning, A Laboratory Manual, 2$^{nd}$ Edition, Cold Spring Harbor Laboratory Press, 14.2–14.35 (1989).
Schuetz et al., *Molecular Pharmacology*, 49: 311–318 (1996).
Sulston, GenBank Accession No. Z73358 (1996).
Underhill et al., *Proc. Natl. Acad. Sci. USA*, 93: 196–200 (1996).
Waye et al., GenBank Accession No. R41114 (1995).
Waye et al., Protein Engineering 8 (Suppl): 90 (Miami Winter Bio Technology Symp. Proc.) 1995.
Wilson et al., GenBank Accession No. U–46669 (1996).
Wilson et al., *Nature*, 368: 32–38 (1994).
Yamazaki et al., *Archives of Biochemistry and Biophysics*, 342(2): 329–337 (1997).
Ziegle et al., *Genomics*, 14: 1026–1031 (1992).
Aoyama et al., *The Journal of Biological Chemistry*, 264(18): 10388–10395 (1989).
Aoyama et al., GenBank Accession No. J04813 (1993).
Aoyama et al., GenBank Accession No. NM000777 (2000).
Ball et al., *Clinical Pharmacology & Therapeutics*, 66(3): 288–294 (1999).
Bork et al., *The Journal of Biological Chemistry*, 264(2): 910–919 (1989).
Brockmoller et al., *Toxicol Lett*, 102–103:173–83 (1998).
Domanski et al., *Molecular Pharmacology*, 59:386–392 (2001).
Dunning et al., *Cancer Epidemiology, Biomarkers & Prevention*, 8: 843–854 (1999).
Finta et al., *Gene*, 260: 13–23 (2000).
Fryer et al., *IARC Sci Publ*, 148: 303–322 (1999).
Gellner et al., GenBank Accession No. AF280107 (2000).
Gonzalez et al., *DNA*, 7(2): 79–86 (1988).
Gonzalez et al., GenBank Accession No. P08684 (1988).
Hashimoto et al., *Eur. J. Biochem.*, 218: 585–595 (1993).
Hashimoto et al., GenBank Accession No. D11131 (2000).
Helzlsouer et al., *Journal of the National Cancer Institute*, 90: 512–518 (1998).
Hengstler et al., *Recent Results Cancer Res.*, 154: 47–85 (1998).
Hilbert et al., *The Journal of Biological Chemistry*, 272(10): 6733–6740 (1997).
Hsieh et al., GenBank Accession No. AF209389 (1999).
Jounaidi, Y., GenBank Accession No. X90579 (1996).
Jounaidi et al., *Biochemical and Biophysical Research Communications*, 205(3): 1741–1747 (1994).
NCBI Annotation Project, GenBank Accession No. XM_011598 (2001).
Peyronneau et al., *Eur. J. Biochem*, 218: 355–361 (1993).
Sachse et al., *Am. J. Hum. Genet.*, 60: 284–295 (1997).
Schuetz et al., *Archives of Biochemistry and Biophysics*, 274(2): 355–365 (1989).
Schuetz, GenBank Accession No. L26985 (1994).
Schuetz et al., GenBank Accession No. L35912 (1996).
Sherif et al., *Cancer Letters*, 107: 229–233 (1996).
Xu et al., *The Journal of Biological Chemistry*, 273(6): 3517–3527 (1998).
Skolnick, *J. Am. Med. Assn.*, 275(8): 581–2 (1996).
Strange et al., *IARC Sci. Publ.*, 148: 231–249 (1999).
Strange et al., *Chem. Biol. Interact*, 24(111–112): 351–364 (1998).
Sulston et al., GenBank Accession No. AC005020 (2000).
Watanabe, M., *Toxicol. Lett*, 28(102–103): 167–171 (1998).
Westlind et al., *Biochemical and Biophysical Research Communications*, 259: 201–205 (1999).
Kuehl, Peter et al., "Sequence diversity in CYP3A promoters and characterization of the genetic basis of polymorphic CYP3A5 expression," *Nature Genetics*, p. 383–391, (Apr. 2001).

* cited by examiner

METHODS FOR EVALUATING THE ABILITY TO METABOLIZE PHARMACEUTICALS

REFERENCE TO RELATED APPLICATION

This application is a continuation-in-part application of U.S. patent application Ser. No. 09/144,367, filed Aug. 31, 1998, now Pat. No. 6,432,639, which is hereby incorporated by reference in its entirety. This application claims the benefit of Provisional Patent Application Ser. No. 60/271,630 filed in the U.S. Patent and Trademark Office on Feb. 26, 2001, which is hereby incorporated by reference in its entirety.

FIELD OF THE INVENTION

The present invention relates to polymorphisms in the cytochrome P450 3A4, cytochrome P450 3A5 and GSTM1 genes and methods for genotyping and phenotyping individuals for such polymorphisms.

BACKGROUND OF THE INVENTION

Cytochrome P450 enzymes are a heme-containing family that play central roles in oxidative, peroxidative and reductive metabolism of numerous endogenous and exogenous compounds, including many pharmaceutical agents. Substances known to be metabolized by P450 enzymes include steroids, bile acids, fatty acids, prostaglandins, leukotrienes, biogenic amines, retinoids, lipid hydroperoxides, phytoalexins, pharmaceuticals, environmental chemicals and pollutants. P450 substrates also include natural plant products involved in flavor, odor and flower color. Many P450 enzymes also have functions in maintaining steady-state levels of endogenous ligands involved in ligand-modulated transcription of genes effecting growth, apoptosis, differentiation, cellular homeostasis, and neuroendocrine functions. The metabolism of foreign chemicals by P450 enzymes can produce toxic metabolites, some of which have been implicated as agents responsible for birth defects and tumor initiation and progression.

The P450 gene superfamily is likely to have evolved from an ancestral gene present before the prokaryote/eukaryote divergence. The number of individual P450 genes in any mammalian species is estimated at 60 to 200. The cytochrome P450 (CYP) 3A subfamily is unique in that it is present in large amounts in human liver microsomes, and there are many forms in the subfamily. Several human cDNAs encoding CYP3A proteins have been identified. The most important of these are CYP3A4, CYP3A5 and CYP3A7. CYP3A4 and CYP3A7 genes are 87% homologous by amino acid and 95% homologous by nucleotide sequence, while CYP3A4 and CYP3A5 are only 88% homologous in the coding region. CYP3A4 and CYP3A7 are 91% homologous in the 5'-flanking sequences, differing by the presence of a unique P450NF specific element (NFSE) and a P450HFLa specific element (HFLaSE), respectively (Hashimoto et al, 1993).

Genetic polymorphisms of cytochrome P450 enzymes result in subpopulations of individuals that are distinct in their ability to perform particular drug biotransformation reactions. These phenotypic distinctions have important implications for selection of drugs. For example, a drug that is safe when administered to the majority of humans may cause intolerable side-effects in an individual suffering from a defect in a cytochrome P450 enzyme required for detoxification of the drug. Alternatively, a drug that is effective in most humans may be ineffective in a particular subpopulation because of the lack of a particular cytochrome P450 enzyme required for conversion of the drug to a metabolically active form. Accordingly, it is important for both drug development and clinical use to screen drugs to determine which cytochrome P450 enzymes are required for activation and/or detoxification of the drug.

It is also important to identify those individuals who are deficient in a particular P450 enzyme. This type of information has been used to advantage in the past for developing genetic assays that predict phenotype and thus predict an individual's ability to metabolize a given drug. Information such as this would be of particular value in determining the likely side effects and therapeutic failures of various drugs and routine phenotyping could be recommended for certain categories of patients.

The CYP3A subclass catalyzes a remarkable number of oxidation reactions of clinically important drugs such as quinidine, warfarin, erythromycin, cyclosporin A, midazolam, lidocain, nifedipine, and dapsone. Current estimates are that more than 60% of clinically used drugs are metabolized by the CYP3A4 enzyme, including such major drug classes as calcium channel blockers, immunosuppressors, macrolide antibiotics and anticancer drugs, see Brian et al., 1990, Biochemistry, vol. 29, pages 11280–11292.

Expression profiles for each member of this family varies significantly. CYP3A4 is expressed in all adult human liver and intestine, accounting for more than 50% of total P450 in both organs. Expression is inducible in vivo and in vitro by numerous compounds such as rifampicin, barbiturates and glucocorticoids. In kidney, CYP3A4 is expressed polymorphically. CYP3A4 expression is sex-influenced, as females have 24% greater expression than males. Substantial interindividual variation in the metabolism of specific compounds by CYP3A4 has been reported (Kleinbloesem et al., Biochemical Pharmacology, 1984, vol. 33, pages 3721–3724. U.S. Pat. No. 6,174,684 to Rebbeck et al. discloses a CYP3A4 variant associated with a heightened risk of developing or having prostate cancer and a decreased risk for developing treatment-related leukemias. The polymorphism disclosed by Rebbeck et al. is an A to G transition in the promoter region of the CYP 3A4 gene which is thought to alter the nifedipine-specific binding element located 287 to 296 bases 5' to the CYP 3A4 transcription start site. The genotype associated with this variant is believed to increase the production of potentially DNA damaging reactive intermediates upon patient exposure to an epipodophyllotoxin. CYP3A5 is detected in 10–30% of Caucasian adult livers, and expressed constitutively in adult kidney. CYP3A5 expression does not appear to be sex-influenced and only moderately inducible by xenobiotics both in vivo and in vitro. CYP3A7 is expressed in fetal liver but only in 25% of adult livers. Molecular mechanisms responsible for the developmentally specific expression of CYP3A's are unknown.

Another supergene family of metabolic enzymes is the glutathione S-transferase (GST) superfamily. These enzymes play an important role in the cellular enzymatic protection against the cytotoxic and mutagenic effects of electrophiles. Thus, GST alleles associated with impaired detoxification will confer an increased susceptibility to a wide range of diseases. In particular, GST genotypes have been associated with an increased susceptibility in diseases associated with oxidative stress. One of the best characterized of such associations is the null mutation in the mu class GSTM1 gene. GSTM1 is polymorphic due to large deletions in the structural gene. The null GSTM1 genotype is clearly associated with bladder cancer and lung cancer, and possibly associated with colorectal, hepatocellular, gastric, esophageal, head and neck as well as cutaneous cancer. There is considerable evidence that the combination of the GSTM1 null genotype in combination with the cytochrome P450 1A1 rare alleles confers a highly increased risk of developing lung cancers in smokers. The GSTM1 null genotype has also been found to be significantly associated with an increased risk of developing postmenopausal breast cancer as described by Helzlsouer et al., J. Natl. Cancer Inst., 1998, vol. 90, pages 512–518.

Women have a 15 percent lifetime risk of developing breast cancer. Approximately 10 to 15 percent of all breast cancers are familial, and approximately 33 percent of these may be linked to genetic mutations. Available treatment options include (1) surgery, (2) radiation therapy, (3) chemotherapy, and (4) hormone manipulation. Hundreds of thousands of women are currently undergoing local, as well as systemic, treatment for their breast cancer. Each treatment has its risks and side effects. The risks and side effects of chemotherapy can be substantially reduced and the likelihood of a successful outcome can be increased if the chemotherapeutic regimen selected is tailored to the individual patient. Two drugs commonly used in the treatment of breast cancer are cyclophosphamide and carmustine (BCNU).

Cyclophosphamide is a nitrogen mustard derivative, polyfunctional alkylating agent which is bioconverted from an inert prodrug to an active DNA alkylating agent by the oxidative cytochromes of the liver of which CYP 3A4 and 3A5 are the principle enzymes. Thus, patients with lower levels of either enzyme will produce less of the active forms of cyclophosphamide when given the same dose over the same time as a patient who has normal levels of these activating enzymes. Cyclophospamide functions to interfere with DNA replication and transcription of RNA, ultimately resulting in the disruption of nucleic acid function. The drug also exhibits potent immunosuppressive activity and phosphorylating properties that enhance its cytotoxicity. In the treatment of breast cancer, cyclophosphamide used alone has been reported to produce objective responses in about 35% of patients. Used in combination regimens, objective responses have been reported in up to 90% of patients, and cyclophosphamide-containing combinations are believed by some experts to be the treatment of choice.

BCNU is a nitrosourea with a broad spectrum of activity. It is a classic alkylating agent, but also inhibits DNA repair by isocyanate formation. BCNU is used alone or as a component of various chemotherapy regimens in the treatment of primary or metastatic tumors. BCNU is a highly toxic drug with a low therapeutic index, thus a therapeutic response is unlikely without some evidence of toxicity. The primary toxicities are pulmonary toxicity and hepatic dysfunction which appear to be dose related. Patients receiving cumulative doses exceeding 1400 mg/m$^2$ are at substantially higher risk than patients receiving lower cumulative doses. Thus, any means of screening prospective cancer patients for factors which can effect the dosing of BCNU is of great importance in effectively designing chemotherapy regimens that include BCNU to enhance the clinical outcome while minimizing adverse effects.

Cisplatin is a bifunctional alkylating agent that binds to DNA and inhibits DNA synthesis. The drug produces predominately DNA interstrand crosslinks with some intrastrand crosslinks resulting from the formation of adducts between activated platinum complexes of the drug. Interstrand crosslinking appears to correlate well with the cytotoxicity of the drug. Cisplatin is used to treat a wide variety of neoplasms and is often used as a component of combination chemotherapeutic regimens because of its relative lack of hematologic toxicity. Cisplatin is a highly toxic drug with a low therapeutic index. While hematologic toxicities such as thrombocytopenia and leukopenia are the major dose-limiting adverse effects of cisplatin therapy, other dose-limiting adverse effects including nephrotoxicity, ototoxicity, neurotoxicity, and emesis are frequently seen. These adverse effects are potentiated in patients receiving other antineoplastic agents or drugs with nephorotoxic or ototoxic effects, such as aminoglycoside antibiotics.

Since the rates of metabolism of drugs and toxins can depend on the amounts and kinds of P450s expressed in a tissue, variation in biological response may be determined by the profile of expression of P450s in each person. As noted above, this variation in response may significantly influence the outcome of treating breast cancer patients with different antineoplastic drugs. Analysis of genetic polymorphisms that lead to altered expression and enzyme activity of these metabolic enzymes are therefore of interest.

SUMMARY OF THE INVENTION

The present invention is directed to novel polymorphisms in the human CYP3A4 and CYP3A5 genes and the detection of polymorphisms in genes encoding the CYP3A4, CYP3A5 and GSTM1 metabolic enzymes in individuals. The polymorphisms detected can influence the outcome of breast cancer treatments and the selection of chemotherapeutic agents used to treat breast cancer in the patients tested. These polymorphisms are predictive of altered metabolism of chemotherapeutic agents used in the treatment of breast cancer and/or the occurrence of disease. According to the present invention there are provided CYP3A4 and CYP3A5 polymorphic nucleic acid sequences and methods to use such nucleic acid sequences and polymorphic GSTM1 sequences, in particular for diagnostic purposes to identify individuals having a polymorphic genotype.

In one embodiment, the present invention is directed to an isolated nucleic acid molecule, comprising a sequence selected from the sequence of SEQ ID NO:1; and the sequence fully complementary thereto. The present invention is also directed to an isolated nucleic acid molecule which includes at least one base variation from that of the human CYP3A4 sequence, wherein the nucleic acid molecule is selected from a nucleic acid molecule that comprises a G nucleotide for an A nucleotide at position −392 of the promoter of said CYP3A4 gene with respect to the start codon of said CYP3A4 gene and at least 17 other bases of said CYP3A4 gene contiguously appurtenant thereto, and a nucleic acid molecule which is fully complementary thereto. In this embodiment, the nucleic acid molecule can include a sequence selected from the group consisting of SEQ ID NO:1, and/or a nucleic acid sequence which is fully complementary to SEQ ID NO:1.

In another embodiment, the present invention is directed to an isolated nucleic acid molecule, comprising a sequence selected from the sequence of SEQ ID NO:2; and the sequence fully complementary thereto. The present invention is also directed to an isolated nucleic acid molecule which includes at least one base variation from that of the human CYP3A5 sequence, wherein the nucleic acid molecule is selected from a nucleic acid molecule that comprises a G nucleotide for an A nucleotide at position −147 of the promoter of said CYP3A5 gene with respect to the start codon of said CYP3A4 gene and at least 33 other bases of said CYP3A5 gene contiguously appurtenant thereto, and a nucleic acid molecule which is fully complementary thereto. In this embodiment, the nucleic acid molecule can include a sequence selected from the group consisting of SEQ ID NO:2 and/or a nucleic acid sequence which is fully complementary to SEQ ID NO:2.

A further embodiment of the present invention includes a method of detecting a variant gene having a polymorphism associated with reduced metabolism of a substrate selected from the group consisting of a CYP3A4 substrate, a CYP3A5 substrate and a GSTM1 substrate in an individual. This method includes obtaining a nucleic acid sample comprising a gene isolated from the individual, the gene being selected from a CYP3A4 gene, a CYP3A5 gene and a GSTM1 gene. The method further includes detecting the presence or absence in the individual of a polymorphism selected from (i) a substitution of a G nucleotide for an A nucleotide at position −392 of the promoter of the CYP3A4 gene with respect to the start codon of the CYP3A4 gene, wherein the presence of the substitution is associated with reduced CYP3A4 substrate metabolism: (ii) a substitution of a G nucleotide for an A nucleotide at position −147 of the promoter of the CYP3A5 gene, wherein the presence of the substitution is associated with reduced CYP3A5 substrate metabolism: and (iii) a GSTM1 null mutation, wherein the presence of the GSTM1 null mutation is associated with reduced GSTM1 substrate metabolism. The method can also include determining whether the individual is homozygous or heterozygous for the polymorphism. A variety of assays are suitable for determining whether any of the identified variant sequences are present. The substrates in question for any one of the three genes can be selected from cyclophosphamide and BCNU.

In a further embodiment, the present invention includes a method for selecting a treatment for a cancer patient. The method the genotyping steps described above and further includes selecting a cancer treatment regime that does not include administration of an anti-cancer agent selected from the group consisting of cyclophosphamide and BCNU if one or more of the polymorphisms are present. A further method for selecting a treatment for a cancer patient can include selecting a cancer treatment regime that includes administration of an anti-cancer agent selected from the group consisting of cyclophosphamide and BCNU if none of the polymorphisms are present.

DETAILED DESCRIPTION OF THE INVENTION

The present invention relates to nucleic acid molecule compositions that contain certain genetic characteristics and methods that identify the presence or absence of such characteristics in patients. The present invention includes the identification of different genetic polymorphisms in the cytochrome P450 3A4, cytochrome P450 3A5 and the GSTM1 genes. The presence or absence of certain polymorphisms in one or more of these genes has been found to be prognostic for a therapeutic response to certain antineoplastic agents. Identification of these polymorphic sequences is used in individuals to screen for altered metabolism of CYP3A4, CYP3A5, and GSTM1 substrates, potential drug-drug interactions, drug adverse effects, likelihood of successful clinical outcome following treatment with cyclophosphamide, cisplatin and/or BCNU.

It is to be understood that this invention is not limited to the particular methodology, protocols, cell lines, animal species or genera, constructs, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a construct" includes a plurality of such constructs and reference to "the CYP3A4 nucleic acid" includes reference to one or more nucleic acids and equivalents thereof known to those skilled in the art, and so forth.

According to the present invention, reference to an "isolated nucleic acid molecule" refers to a nucleic acid molecule which is the size of or smaller than a gene. Thus, an isolated nucleic acid molecule does not encompass isolated genomic DNA or an isolated chromosome. The term isolated nucleic acid molecule does not connote any specific minimum length. It should also be appreciated that reference to an isolated nucleic acid molecule does not necessarily reflect the extent of purity of the nucleic acid molecule. An isolated nucleic acid molecule of the present invention can be obtained from a natural source, such as a tissue sample, or it can be produced using molecular biology techniques, such as by PCR amplification, or it can be produced by chemical synthesis.

"Allele" has the meaning which is commonly known in the art, that is, a genomic variant of a referent gene, including variants, which, when translated result in functional or dysfunctional (including non-existant) gene products. The first identified allelic form is arbitrarily designated as the reference form and other allelic forms are designated as alternative or variant alleles. The allelic form occurring most frequently in a selected population is sometimes referred to as the wildtype form.

"Contiguously appurtenant to" means any bases flanking the referent position, including the instances of all bases selected 5' to the referent position and no bases selected 3' to the referent position; all bases selected 3' to the referent position and no bases selected 5' to the referent position; and some bases selected 5' and some bases selected 3' to the referent position. The term is intended to mean that the selected bases necessarily must be in the same sequential order as described in the referent sequence, with the exception of the variant base at the referent position.

"For the purpose of determining genotype" means that one of the purposes is to determine genotype, not necessarily that the end goal or use of the information is to determine genotype. For instance, "for the purpose of determining genotype" includes the use of the information to determine genotype for the ultimate goal of determining probability of negative or positive drug interactions.

"Gene" has the meaning that is commonly-known in the art, that is, a nucleic acid sequence that includes the translated sequences that code for a protein ("exons") and the untranslated intervening sequences ("introns"), and any regulatory elements ordinarily necessary to translate the protein.

"Genotype" has the meaning that is commonly-known in the art, that is, a physical description of a nucleic acid sequence.

"Hybridization" has the meaning that is commonly-known in the art, that is, the formation of a duplex structure by two single-stranded nucleic acids due to complementary base pairing. Hybridization can occur between exactly complementary nucleic acid strands or between nucleic acid strands that contain some regions of mismatch.

"Polymorphism" means a polymorphism wherein the group exists by virtue of a difference in identity of one or more nucleotides at given sequence locations. The location of nucleotide identity differences is usually preceded by and followed by highly conserved sequences (e.g., sequences that vary in less than 1/100 or 1/1000 members of the populations). However, more than one single nucleotide polymorphism can exist between or among the group members. A "transition" is the replacement of one purine by another purine or one pyrimidine by another pyrimidine. A "transversion" is the replacement of a purine by a pyrimidine or vice versa. Single nucleotide polymorphisms can also arise from a deletion of a nucleotide or an insertion of a nucleotide relative to a given sequence location.

"Stringent hybridization" means that which is commonly-known in the art, that is, at a salt concentration of no more than 1M and a temperature of at least 25 degrees Celsius. For example, conditions of 5×SSPE (750 mM NaCl, 50 mM Sodium Phosphate, 5 mM EDTA, pH 7.4) and a temperature of 55 degrees to 60 degrees Celsius are suitable.

"Substrate" means a chemical entity that is modified by activity of a CYP3A4, CYP3A5 and/or GSTM1 enzyme, usually under normal physiological conditions. Most of these substrates are lipophilic compounds. Although the duration of drug action tends to be shortened by metabolic transformation, drug metabolism is not "detoxification." Frequently the metabolic product has greater biologic activity than the drug itself. In some cases the desirable pharmacologic actions are entirely attributable to metabolites, the administered drugs themselves being inert. Likewise, the toxic side effects of some drugs may be due in whole or in part to metabolic products. The range of known substrates for CYP3A4, CYP3A5 and GSTM1 is very broad. In a preferred embodiment, a substrate of any one or more of CYP3A4, CYP3A5 and GSTM1 is selected from the group consisting of cyclophosphamide, cisplatin and BCNU. In a further preferred embodiment, a substrate of any one or more of CYP3A4, CYP3A5 and GSTM1 is selected from the group consisting of cyclophosphamide and BCNU.

All technical and scientific terms used herein have the same meaning as commonly understood to one of ordinary skill in the art to which this invention belongs unless clearly indicated otherwise.

In the present invention, alleles are expressed by symbols in accordance with definitions given by IUPAC-IUB and common names or common usage in the art. One embodiment of the present invention is an isolated nucleic acid molecule comprising a CYP3A4 sequence polymorphism of SEQ ID NO:1 as part of other than a naturally occurring chromosome, as described in detail below. Another embodiment of the present invention is an isolated nucleic acid molecule comprising a CYP3A5 sequence polymorphism of SEQ ID NO:2 as part of the other than a naturally occurring chromosome. In accordance with the present invention, an isolated nucleic acid molecule is a nucleic acid molecule that has been removed from its natural milieu (i.e., that has been subject to human manipulation) and can include DNA, RNA, or derivatives of either DNA or RNA. An isolated nucleic acid molecule of the present invention can be isolated from its natural source or can be produced using recombinant DNA technology (e.g., polymerase chain reaction (PCR) amplification, cloning) or chemical synthesis. The nucleic acid molecules of the present invention are isolated and obtained in substantial purity, generally as other than an intact chromosome. Usually, the nucleic acid molecule will be obtained substantially free of other nucleic acid sequences, generally being at least about 50%, usually at least about 90% pure. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably.

The nucleic acid sequence of the CYP3A4 gene is known in the art and accessible in public databases. Genbank Accession No. D11131 provides a partial sequence of the human cytochrome P450 3A4 gene. Genbank Accession No. M18907 (cDNA) provides the cDNA sequence of a human CYP3A4 allele. The promoter region of the CYP3A4 gene is provided as SEQ ID NO:3.

The nucleic acid sequence of the CYP3A5 gene is generally known in the art and accessible in public databases. For example, Genbank Accession No. S74699 provides the CYP3A5 5' genomic region. However, the present inventors have sequenced a portion of the promoter region and exon 1 of the CYP3A5 gene and found errors in Genbank Accession No. S74699. The correct sequence for the portion of the promoter and exon 1 is provided as SEQ ID NO:4.

The nucleic acid sequence of the GSTM1 gene is known in the art and accessible in public databases. The null mutation in the mu class GSTM1 gene is well known in the art. For example, see Xu, S.; Wang, Y.; Roe, B.; Pearson, W. R.: Characterization of the human class mu glutathione S-transferase gene cluster and the GSTM1 deletion. J. Biol. Chem. 273: 3517–3527, 1998.

As used herein, the term "CYP3A4 gene," "CYP3A5 gene" or "GSTM1 gene" is intended to refer to both the wildtype and polymorphic sequences, unless specifically denoted otherwise. Nucleic acids of particular interest comprise the provided polymorphic sequences. It is within the skill of one in the art to identify the location of a polymorphic sequence of the present invention using wildtype CYP3A4, CYP3A5 or GSTM1 genomic or cDNA sequences known in the art. A skilled artisan can use a polymorphic sequence, its corresponding wildtype sequence and the CYP3A4, CYP3A5 or GSTM1 sequence contiguously appertanant to the referenced polymorphism to determine the position of the polymorphism. The positions of the CYP3A4 and CYP3A5 polymorphisms of the present inventions are described below in Table 1.

TABLE 1

| GENE | TYPE | SEQ ID NO: | SEQUENCE |
|---|---|---|---|
| CYP3A4 | WT | 5 | GACAAGGGCAAGAGAGAG |
|  | PM | 1 | GACAAGGGCAGGACAGAG |
| CYP3A5 | WT | 6 | CGATTCTTTGCTACTGGCTGCAGCTGCAGCCCCA |
|  | PM | 2 | CGATTCTTTGCTACTGGCTGCAGCTGCAGCCCCG |

In accordance with the present invention, the polymorphism of the CYP3A4 sequence occurs at nucleotide −392 of the promotor region of the CYP3A4 genomic sequence. Sequences in the promoter region are denoted by negative numbers corresponding to the number of nucleotides 5' to the start codon. The start codon of the CYP3A4 gene is at nucleotides 1208–1210 of SEQ ID NO:3. The polymorphism is a base pair substitution of A to G. The polymorphism is in the promoter region so it does not result in an amino acid substitution. This CYP3A4 polymorphism is described in detail in WO 9913106A1, published Mar. 18, 1999 and is identified in SEQ ID NO:44 therein. In addition, the CYP3A4 polymorphism can be identified as an A to G transition at position −290 with reference to the transcription initiation site. More particularly, the CYP3A4 polymorphism occurs at nucleotide 816 of SEQ ID NO:3. One embodiment of the present invention is an isolated nucleic acid molecule that comprises the foregoing human cytochrome P450 3A4 polymorphism. Such an isolated nucleic acid molecule includes the polymorphism and at least 17 other bases, alternatively at least 20 other bases, at least 30 other bases, at least 40 other bases, or at least 50 other bases of the wildtype sequence contiguously appurtenant thereto. Further, the present invention includes human CYP3A4 alleles that comprise the CYP3A4 polymorphism as described herein, having appurtenant sequences of 10, 15, 20, 25, 30, 35, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, or 1000 bases, or any whole number encompassed by the range of 1–10,000. Further embodiments of the present invention include nucleic acid molecules having a sequence fully complementary to any of the sequences described above.

In accordance with the present invention, the polymorphism of the CYP3A5 sequence occurs at nucleotide −147 of the promotor region of the CYP3A5 genomic sequence. Sequences in the promotor region are denoted by negative numbers corresponding to the number of nucleotides 5' to the start codon. The start codon of the CYP3A5 gene is at nucleotides 1184–1186 of SEQ ID NO:4. The polymorphism is a base pair substitution of A to G. The polymorphism is in the promoter region so it does not result in an amino acid substitution. In addition, the CYP3A5 polymorphism can be identified as an A to G transition at position −44 with reference to the transcription initiation site. More particularly, the CYP3A5 polymorphism occurs at nucleotide 1037 of SEQ ID NO:4. One embodiment of the present invention is an isolated nucleic acid molecule that comprises the foregoing human cytochrome P450 3A5 polymorphism. Such an isolated nucleic acid molecule includes the polymorphism and at least 33 other bases, alternatively at least 40 other bases, or at least 50 other bases of the wildtype sequence contiguously appurtenant thereto. Further, the present invention includes human CYP3A5 alleles that comprise the CYP3A5 polymorphism as described herein, having appurtenant sequences of 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, or 1000 bases, or any whole number encompassed by the range of 1–10,000. Further embodiments of the present invention include nucleic acid molecules having a sequence fully complementary to any of the sequences described above.

In accordance with the present invention, the polymorphism of the GSTM1 gene is the well-characterized null mutation.

The genotype of an individual is determined with respect to the provided CYP3A4, CYP3A5 and/or GSTM1 gene polymorphisms. The genotype is useful for determining the presence of phenotypically evident polymorphism having the effect of reduced metabolism of a CYP3A4, CYP3A5 or GSTM1 substrate, respectively.

One embodiment of the present invention is a method of identifying a sample containing a nucleic acid molecule that comprises a wildtype or variant allele, the method comprising identifying the presence or absence of one or more of the CYP3A4, CYP3A5 or GSTM1 polymorphisms described herein.

Many of the diagnostic assays rely on amplification of part or all of a CYP3A4, CYP3A5 and/or GSTM1 nucleic acid molecule. In one embodiment, portions of a nucleic acid molecule are amplified by the polymerase chain reaction (PCR). The PCR process is described in e.g., U.S. Pat. Nos. 4,683,195; 4,683,202; and 4,965,188; PCR Technology:Principles and Applications for DNA Amplification (ed. Erlich, Freeman Press, New York, N.Y., 1992); PCR Protocols: A Guide to Methods and Applications (eds. Innis et al., Academic Press, San Diego, Calif. (1990); Mattila et al. Nucleic Acids Res. 19:4967 (1991); Eckert & Kunkel PCR Methods and Applications 1:17 (1991); PCR (eds. McPherson et al., IRL Press, Oxford), each of which is incorporated by this reference in its entirety.

To amplify a portion of a nucleic acid molecule in accordance with the present invention in a sample by PCR, the sequence must be accessible to the components of the amplification system. Accessibility can be achieved by isolating nucleic acid molecules from the sample. A variety of techniques for extracting nucleic acid molecules from biological samples are known in the art. Alternatively, if the sample is fairly readily disruptable, the nucleic acid need not be purified prior to amplification by the PCR technique, i.e., if the sample comprises cells, particularly peripheral blood lymphocytes or monocytes, lysis and dispersion of the intracellular components may be accomplished merely by suspending the cells in hypotonic buffer. See Han et al., Biochemistry, 1987, vol. 26, pages 1617–1625. Polymorphisms are detected in a nucleic acid molecule from an individual being analyzed. For assay of genomic DNA, virtually any biological sample (other than pure red blood cells) is suitable. Examples of convenient tissue samples include whole blood, semen, saliva, tears, urine, fecal material, sweat, buccal, skin and hair. Nucleic acid molecules can be obtained according to procedures well-known in the art.

For amplification of mRNA sequences, a first step is the synthesis of a DNA copy (cDNA) of the region to be amplified by reverse transcription. Reverse transcription is the polymerization of deoxynucleoside triphosphates to form primer extension products that are complementary to a ribonucleic acid template. The process is effected by reverse transcriptase, an enzyme that initiates synthesis at the 3'-end of the primer and proceeds toward the 5'-end of the template until synthesis terminates. Examples of suitable polymerizing agents that convert the RNA nucleic acid molecule into a complementary, cDNA sequence are avian myeloblastosis virus reverse transcriptase and *Thermus thermophilous* DNA polymerase. Reverse transcription can be carried out as a separate step, or in a homogeneous reverse transcription-polymerase chain reaction (RT-PCR). Polymerizing agents suitable for synthesizing a cDNA sequence from the RNA template are reverse transcriptase (RT), such as avian myeloblastosis virus RT, Moloney murine leukemia virus RT, or *Thermus thermophilous* DNA polymerase.

Primers for PCR amplification are designed so that the position at which each primer hybridizes along a duplex sequence is such that an extension product synthesized from one primer, when separated from the template (complement), serves as a template for the extension of the other primer. The primers are selected to be substantially complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer with the remainder of the primer sequence being complementary to the strand. Alternatively, complementary bases or longer sequences can be interspersed into the primer, provided that the primer sequence has sufficient complementarity with the sequence of the strand to be amplified to hybridize therewith and thereby form a template for synthesis of the extension product of the other primer. Paired primers for amplification of a given segment of DNA are designated forward and reverse primers. The forward primer hybridizes to a double-stranded DNA molecule at a position 5', or upstream, from the reverse primer. The forward primer hybridizes to the complement of the coding strand of the double stranded sequence, i.e., the antisense strand, and the reverse primer hybridizes to the coding strand.

The appropriate length of a primer depends on the intended use of the primer but typically ranges from about 10 to about 100, preferably about 15 to about 50, more preferably about 15 to about 30, or more preferably about 15 to about 25 nucleotides in length. The spacing of primers determines the length of segment to be amplified. The spacing is not usually critical and amplified segments can range in size from about 25 bases to at least about 35 kilobases in length. Segments from about 25 to about 2000, preferably about 50 to about 1000, more preferably about 100 to about 500 nucleotides in length are typical.

A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

Other suitable amplification methods include the ligase chain reaction (LCR) (see Wu and Wallace, Genomics, 1989, vol. 4, pages 560; Landegren et al., Science, 1988, vol. 241, pages 1077; transcription amplification (Kwoh et al., Proc. Natl. Acad. Sci. USA, 1989, vol. 86, page 1173), and self-sustained sequence replication (Guatelli et al., Proc. Nat. Acad. Sci. USA, 1990, vol. 87, page 1874) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

An allele-specific primer can be used in a PCR amplification. The allele-specific primer hybridizes to a site on a nucleic acid molecule that overlaps with a polymorphism and extension will only occur if an allelic form complementary to the primer is present. See Gibbs, Nucleic Acid Res., 1989, vol. 17, pages 2427–2448. This primer is used in conjunction with a second primer which hybridizes at a distal site. Amplification proceeds from the two primers leading to a detectable product signifying the particular allelic form is present. Thus, the presence or absence of an amplification product is detected using standard methods. Controls can be used that test the efficacy of the amplification reaction itself or that allow the experimental results to be compared with known wildtype or polymorphic CYP3A4, CYP3A5 and/or GSTM1 nucleic acid molecule samples. The method works best when the mismatch is included in the 3'-most position of the oligonucleotide aligned with the polymorphism because this position is most destabilizing to elongation from the primer.

Sample nucleic acid molecules, isolated directly from cells, amplified or cloned fragments, can also be analyzed by a number of other methods known in the art. The nucleic acid molecule can be sequenced by using either the dideoxy chain termination method or other methods (see for example Sambrook et al., Molecular Cloning, A Laboratory Manual (2nd Ed., CSHP, New York 1989); Zyskind et al., Recombinant DNA Laboratory Manual, (Acad. Press, 1988)).

Hybridization using allele-specific probes, described by e.g., Saiki et al., Nature 324, 163–166 (1986); Dattagupta, EP 235,726, Saiki, WO 89/11548, can be used to determine the presence or absence of a polymorphism by, for example Southern blot, dot blots, etc. An allele-specific probe can be designed that hybridizes to a segment of a nucleic acid molecule from one individual but does not hybridize to the corresponding segment from another individual due to the presence of different polymorphic forms in the two individuals. Hybridization conditions should be sufficiently stringent that there is a significant difference in hybridization intensity between alleles.

The hybridization pattern of a control and variant sequence to an array of oligonucleotide probes immobilized on a solid support, as described in U.S. Pat. No. 5,445,934, or in WO 95/35505, can also be used as a means of detecting the presence of variant sequences.

Amplification products generated using the polymerase chain reaction can be analyzed by the use of denaturing gradient gel electrophoresis (DGGE). Different alleles can be identified based on the different sequence-dependent melting properties and electrophoretic migration of DNA in solution. Erlich, ed., PCR Technology, Principles and Applications for DNA Amplification, (W. H. Freeman and Co, New York, 1992), Chapter 7.

Alleles of target sequences can be differentiated using single-strand conformation polymorphism analysis (SSCP), which identifies base differences by alteration in electrophoretic migration of single stranded PCR products, as described in Orita et al., Proc. Nat. Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Other methods of detection include mismatch cleavage detection and heteroduplex analysis in gel matrices. These methods are used to detect conformational changes created by DNA sequence variation as alterations in electrophoretic mobility. Alternatively, where a polymorphism creates or destroys a recognition site for a restriction endonuclease, referred to as restriction length polymorphism, or RFLP, the sample is digested with that endonuclease and the products size fractionated to determine whether the fragment was digested. Fractionation is performed by gel or capillary electrophoresis, particularly acrylamide or agarose gels.

In one embodiment of the present invention, an array of oligonucleotides are provided, where discrete positions on the array are complementary to one or more of the provided polymorphic sequences, e.g. oligonulcoetides of at least 12 nucleotides, frequently 20 nucleotides or larger and including the sequence flanking the polymorphic position. Such an array may comprise a series of oligonucleotides, each of which can specifically hybridize to a different polymorphism. For examples of arrays, see Hacia et al., 1996, Nat.

Genet., vol. 14, pages 441–447 and DeRisi et al., 1996, Nat. Genet., vol. 14, pages 457–460. Arrays of interest may further comprise sequences, including polymorphisms, of other genetic sequences, particularly other sequences of interest for pharmacogenetic screening.

It is within the scope of the present invention that one or more CYP3A4, CYP3A5 and GSTM1 polymorphisms provided herein can be detected in a single assay such as a multiplex assay to identify the presence or absence of different alleles in the same assay, see for example Stuven et al, Pharmacogenetics, 1996, vol. 6, pages 417–421.

According to the present invention, a polymorphism provided herein is indicative of a poor clinical outcome of breast cancer treatment using cyclophosphamide, BCNU or combinations of these drugs together or in combination with other chemotherapeutic regimens.

A preferred strategy for analysis entails amplification of a DNA sequence spanning the polymorphism, in the instance of CYP3A4 or CYP3A5 polymorphisms of the present invention. Amplification of such a sequence can be primed from forward and reverse primers that hybridize to a CYP3A4 or CYP3A5 gene on opposite sides of the polymorphism but which do not hybridize to the variant nucleotide sequence itself. That is, for detection of the polymorphism, the forward primer hybridizes upstream or 5' to the polymorphic site and the reverse primer hybridizes downstream or 3' to this site. The forward primer is sufficiently complementary to the antisense strand of a nucleic acid molecule to hybridize therewith and the reverse primer is sufficiently complementary to the sense strand of the sequence to hybridize therewith. The primers usually comprise first and second subsequences from opposite strands of a double-stranded DNA sequence. It is particularly important to avoid mismatches in the two nucleotides at the 3' end of the primer (especially the terminal nucleotide). Having amplified a segment of a gene known to span a polymorphism, a variety of assays are available for determining whether the polymorphism is present that are disclosed herein, preferably, using allele specific primers. For example, selective amplification of the wildtype allele of the gene in question allele can be accomplished using a forward primer that has about 10–50, and usually 15–30 nucleotides from the wildtype genomic sequence, including the portion of the gene corresponding to the position of the polymorphism. Such a forward primer when paired with any suitable reverse primer downstream from the polymorphic nucleotide sequence (i.e., sufficiently complementary to the sense strand of gene to hybridize therewith) can be used to amplify selectively the wildtype allele without amplifying a mutant allele. The polymorphic nucleotide sequence usually occurs near, or preferably at, the 3' end of the primer. The same result can be achieved by using a reverse primer that has about 10–50 or usually 15–30 contiguous nucleotides from the complement of the wildtype genomic sequence (i.e., the antisense strand) including the polymorphic nucleotide sequence. Such a reverse primer can be paired with any suitable forward primer sufficiently complementary to a sequence of the antisense strand of the gene upstream from the polymorphic nucleotide sequence to hybridize therewith. The position corresponding to the polymorphic nucleotide sequence should again be at or near the 3' end of the reverse primer. For selective amplification of a mutant allele a suitable forward primer for amplification comprises about 10–50 or usually 15–30 contiguous nucleotides including a polymorphic nucleotide sequence from the mutant genomic sequence (i.e., the sense strand). The forward primer can be paired with any suitable reverse primer sufficiently complementary to the sense strand of a genomic subsequence downstream from the polymorphic nucleotide sequence to hybridize therewith. Alternatively, the same result can be achieved using a reverse primer comprising about 10–50 or 15–30 contiguous nucleotides including the polymorphic nucleotide sequence from the complement of the mutant sequence (i.e., the antisense strand). Such a reverse primer can be paired with any suitable forward primer sufficiently complementary to the antisense strand of a subsequence upstream from a polymorphic nucleotide sequence to hybridize therewith.

Following amplification, the sample under test is characterized as wildtype or mutant by the presence or absence of an amplification product. With a primer designed for selective amplification of the wildtype allele, the presence of an amplification product is indicative of that allele and the absence of an amplification product indicative of a mutant allele. The converse applies for primers designed for selective amplification of a mutant allele. In preferred assay, a sample is divided into two aliquots, one of which is amplified using primers for wildtype allele amplification, the other of which is amplified using primers appropriate for mutant allele amplification. The presence of an amplification product in one but not both of the aliquots indicates that the individual under test is either wildtype or a homozygous for the mutation (depending on aliquot in which the amplification product occurred). The presence of amplification product in both aliquots indicates that the individual is heterozygous. The absence of an amplification product in both aliquots would indicate either the absence of a gene or a quality control problem in the amplification procedure requiring that the assay be repeated. The presence or absence of amplification products can be detected by gel electrophoresis using methods standard in the art or described herein.

In the case of the GSTM1 null mutation, a preferred strategy for analysis entails amplification using any portion of sequence in the coding region of the GSTM1 gene that would produce a detectable PCR product if the gene is wildtype, but no PCR product if the null mutation is present. Although some conventional methods for determining hetero- or homozygosity, such as that described above, would not be useful for the GSTM1 null mutation, those skilled in the art could design suitable methods. For example, one could conduct an assay in which two differently sized PCR amplification products would be produced for a heterozygote. Such an assay could be designed once the breakpoints for the null mutation were determined.

In further preferred embodiments of the present invention, the various genotyping methods described herein can be used in a method for selecting a treatment for a cancer patient. As described below in the examples, the polymorphisms of the present invention have been associated with reduced metabolism of various chemotherapeutic agents, specifically cyclophosphamide and BCNU. Thus, in such a method for selecting a treatment for a cancer patient, if one or more of the polymorphisms are present, a cancer treatment regime is selected to account for the phenotypic result of the identified genotype. More particularly, a cancer treatment regime can be selected that does not include administration of an anti-cancer agent that is metabolized by an expression product of one of the genes described herein, and particularly, cyclophosphamide and BCNU. Alternatively, a cancer treatment regime can be selected that includes administering an anti-cancer agent that is metabolized by an expression product of one of the genes described herein at higher than conventional doses. More particularly, such doses can be at least about 1% higher than conventional doses, more preferably, at least about 10% higher than conventional doses, and even more preferably, at least about 50% higher than conventional doses. Conventional doses of known chemotherapeutic agents are well-known to those of skill in the art. More particularly, conventional doses of cyclophosphamide can include 40–100 mg/Kg. Conventional doses of BCNU can include 100–200 mg/m² every 6 weeks. In an alternative method for selecting a treatment for a cancer patient using one of the various genotyping methods described herein, if the patient is identified as having none of the three polymorphisms of the present invention, a cancer treatment regime that includes administration of an anti-cancer agent selected from the group consisting of cyclophosphamide and BCNU is selected. More particularly, this method includes administration of one of such anti-cancer agents at conventional doses.

One embodiment of the present invention is a diagnostic kit. The kit comprises useful components for practicing the methods of the present invention. The kit typically comprises at least one of the primers needed for the PCR amplification if PCR amplification is used and also control DNA suitable for determining the success of the PCR reaction and/or to confirm the identification of the presence or absence of a polymorphism in a sample. A kit usually contains a matched pair of forward and reverse primers as described above for amplifying a segment encompassing a polymorphism of the present invention. For selective amplification of mutant or wildtype alleles, kits usually contain a pair of primers for amplification of the mutant allele and/or a separate pair of primers for amplification of the wildtype allele. Optional additional components of the kit include, for example, restriction enzymes for analysis of amplification products, reverse-transcriptase or polymerase, the substrate nucleoside triphosphates, and the appropriate buffers for reverse transcription, PCR, or restriction enzyme reactions. Usually, the kit also contains instructions for carrying out the methods.

The method of the present invention is characterized by detecting the polymorphisms provided herein, and is useful in gene diagnosis for detecting CYP3A4, CYP3A5 and/or GSTM1 gene polymorphisms. As long as the method is capable of detecting the aforementioned specific types of mutation which are clearly defined and characterized by the present invention, no limitation is imposed on the techniques to be employed in the method. For example, a variety of routine methods may be widely used. Since the types of gene mutation to be detected by the present invention are now clarified and specified, it would be obvious for skilled persons in the art to adopt another suitable method. For detecting them from the reading of the disclosure of this specification.

Also provided are databases comprising sequence information pertaining to at least one the polymorphisms of the present invention. Software programs comprising use of a database of the present invention are also included.

In another embodiment, said method further comprises digesting DNA encoding at least a part of the nucleic acid sequence containing the polymorphism with a restriction enzyme that will cut, or will not cut, at or adjacent to one of the polymorphic positions according to whether the polymorphism is present. Those methods wherein said nucleic acid is amplified prior to the digestion step are preferred. The materials useful for these methods can be obtained as described, and these methods can be accomplished as discussed.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

The following examples are provided for the purposes of illustration and are not intended to limit the scope of the present invention.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some allowance should be made for experimental errors and deviations. Unless otherwise indicated, parts are parts by weight, molecular weight is average molecular weight, temperature is in degrees centigrade; and pressure is at or near atmospheric.

EXAMPLE 1

This example describes the identification of a variant of the known cytochrome P450 3A5 sequence (CYP4503A5).

Blood specimens from 32 individuals were collected after obtaining informed consent. All samples were stripped of personal identifiers to maintain confidentiality. The only data associated with the sample were self-reported gender and racial group designations. Of the 32 individuals, 10 were African Americans, 10 were Caucasians, 6 were Japanese and 6 were Chinese. Genomic DNA was isolated using standard methods. Polymerase chain reaction (PCR) amplification of regions of the CYP4503A5 gene were performed using the primers listed in Table 2. The PCR amplification was performed in a total reaction volume of 50 microliters (µl). The final magnesium chloride concentration (2 mM) was optimized empirically. The final genomic DNA concentration was about 100 nanogram (ng) per reaction from 2 individuals. The PCR reactions were performed using Perkin Elmer GENEAMP® PCR kit (available from Perkin Elmer, Norwalk, Conn.) using Taq Gold DNA polymerase according to manufacturer's instructions and using the following primers.

TABLE 2

PCR Primers

| Region | Forward/Reverse | SEQ ID NO: | 5'–3' |
|---|---|---|---|
| 3A5 | Forward | 7 | GCAGGTCATTATGTTAGGT |
| 3A5 | Reverse | 8 | CCTTCTTCAACTGTCTCCT |

Thermal cycling was performed with an initial denaturation step at 94° C. for 10 min, followed by 40 cycles of denaturation at 95° C. for 30 sec, primer annealing at 55° C. for 45 sec, and primer extension at 72° C. for 2 min, followed by final extension at 72° C. for 5 min.

The resulting PCR products were purified using MICROCON®-100 columns (available (avaliable from Millipore, Bedford, Mass.). PCR products from two individuals were combined for each cycle of sequencing. Cycle sequencing was performed on the GENEAMP® PCR System 9600 PCR machine using the ABI PRISM® dRhodamine Terminator Cycle Sequencing Ready Reaction Kit (available from Applied Biosystems, Inc., Foster City, Calif.) according to the manufacturer's directions. Oligonucleotide primers used for the sequencing reactions include those shown in Table 3.

TABLE 3

Sequencing Primers

| Region | Forward/Reverse | SEQ ID NO: | 5'—3' |
| --- | --- | --- | --- |
| 3A5 | Forward | 9 | GCAGGTCATTATGTTAGGT |
|  | Forward | 10 | CTGATACATAGTTATCTTCCTTG |
|  | Forward | 11 | CAAGTCAACTCCACCAAC |
|  | Forward | 12 | GGGCACAAGTACACTCC |
|  | Reverse | 13 | AACATAGATGAAGAGACTTACCTG |
|  | Reverse | 14 | CTAAGGGCACAGTCTGG |
|  | Reverse | 15 | TTCCAGAATACTTGAAATCC |
|  | Reverse | 16 | TGTGCTGTTGTTTGCTG |

About 8 µl sequencing reactions were subjected to 30 cycles at 96° C. for 20 sec, 50° C. for 20 sec, and 60° C. for 4 min, followed by ethanol precipitation. Samples were evaporated to dryness at 50° C. for about 15 min and resuspended in 2 µl of loading buffer (5:1 deionized formamide:50 mM EDTA pH 8.0), heated to 65° C. for 5 min, and electrophoresed through 4% polyacrylamide/6M urea gels in an ABI 377 Nucleic Acid Analyzer according to the manufacturer's instructions for to obtain sequence information. All sequences were determined from both the 5' and 3' (sense and antisense) direction. The 16 electropherograms were analyzed by comparing peak heights, looking for about 25% reduction in peak size and/or presence of extra peaks as an indication of heterozygosity.

A sequence comprising a polymorphism identified from the sequencing is shown below the corresponding wildtype sequence, both the polymorphic nucleotide and the corresponding wildtype nucleotide at the same position are shown in bold, and are listed below in Table 4. For example, a variation of a A to a G transition was discovered at base pair −147 in the promoter region of the CYP4503A5 gene.

TABLE 4

Newly Identified CYP4503A5 Gene Polymorphism

| Location | SEQ ID NO | Polymorphism Sequence |
| --- | --- | --- |
| Promoter−147 | 6 | CGATTCTTTGCTACTGGCTGCAGCTGCAGCC CCA |

TABLE 4-continued

Newly Identified CYP4503A5 Gene Polymorphism

| Location | SEQ ID NO | Polymorphism Sequence |
| --- | --- | --- |
|  | 2 | CGATTCTTTGCTACTGGCTGCAGCTGCAGCC CCG |

SEQ ID NO:4 lists the sequence of the reference CYP4503A5 gene, includes a portion of the promoter and exon 1.

EXAMPLE 2

This example describes the association of the Promoter −392 CYP4503A4 polymorphism with survival rate of breast cancer patients receiving treatment with the chemotherapy drugs cyclophosphamide, cisplatin and 1,3-bis-(chloroethyl)-1-nitrosourea.

Genomic DNA was isolated from peripheral blood lymphocytes of 86 chemotherapy naive female patients with metastatic or inflammatory breast cancer who participated in a trial for high-dose cyclophosphamide (CY), cisplatin and 1,3-bis-(chloroethyl)-1-nitrosourea (BCNU) chemotherapy with breast cancer using standard methods. DNA from each patient was genotyped for the Promoter −392 CYP4503A4 single nucleotide polymorphisms (SNPs) in the CYP3A4 gene. TAQMAN® assays were performed using DNA samples from each individual to identify the presence or absence of the Promoter −392 CYP4503A4 variant. The primers identified in Table 5 were used:

TABLE 5

PCR Primers

| PCR Primer | SEQ ID NO: | Primer Sequence |
| --- | --- | --- |
| 3A4-392 forward | 17 | ATCTGTAGGTGTGGCTTGTTGG |
| 3A4-392 reverse | 18 | TATCAGAAACTCAAGTGGAGCCAT |

PCR amplification was performed using 1× Perkin-Elmer TAQMAN® Reagent Mix #43C4447, about 900 nM 3A4-392 for primer, about 900 nM 3A4-392 rev primer, about 200 nM normal FAM™-labeled probe having the nucleic acid sequence 5'-AGAGACAAGGGCAAGAGAGAGGCGAT-3' (SEQ ID NO:19), and 200 nM variant TET™-labeled probe having the nucleic acid sequence 5'-GACAAGGGCAGGAGAGAGGCGA-3' (SEQ ID NO:20). Thermal cycling was performed at an initial temperature of 50° C. for 2 min followed by a denaturation step at 95° C. for 10 min, followed by 40 cycles of denaturation at 94° C. for 30 sec, primer annealing and extension was performed at 60° C. 30 sec. The fluorescence resulting from the release of labeled probe during PCR amplification and probe hybridization was measured using a fluorometer and the ratio of FAM™ to TET™ fluorescence was calculated to determine the occurrence of the polymorphic site and homo- or heterozygosity compared to sequenced controls.

The results correlating survival with treatment are shown below in Table 6. Patients carrying the variant for CYP3A4 demonstrated significantly higher blood concentrations of CY on day 2 (p=0.0260) and day 3 (p=0.0247). Apparent induction of CY metabolism (Day 3 exposure/Day 1 exposure) was also higher among those carrying the variant SNP (p=0.0260). Median survival for patients carrying the promoter −392 CYP3A4 polymorphism was about 1.6 years compared to about 2.9 years for patients without the variant.

TABLE 6

CYP4503A4 Variants and Survival. The A allele is wildtype and the B allele is mutant.

| Survival >3 years | AA | AB or BB | Total |
|---|---|---|---|
| No | 31(48.3%) | 11 (84.6%) | 42 |
| Yes | 27(51.3%) | 2(15.44) | 29 |
| Total | 58 | 13 | 71 |

| Mutation Carrier | Median Survival Rate (Years) | 95% Confidence Interval (years) | |
|---|---|---|---|
| | | Lower Bound | Upper Bound |
| No | 2.88 | 1.89 | 4.42 |
| Yes | 1.64 | 0.88 | 2.43 |
| p-value | 0.0476 | | |

The results indicate that persons who are homozygous for the A allele have lower blood concentrations of CY and subsequently a 46.6% survival rate beyond 3 years compared to a 15.4% survival rate for those women who have the B allele. Thus, breast cancer patients who have the B allele have higher concentrations of CY and about a ⅓ chance of survival when treated with CY than patients that are homozygous for the A allele. The data suggests that the Promoter −392 variation is detrimental to successful treatment with CY and patients with tumors for which CY treatment is typically used can be genotyped, i.e. screened, as candidates for treatment with CY. Those patients with the B allele, either AB or BB genotypes, will be less likely to benefit from treatment with CY.

EXAMPLE 3

This example describes the association of the Promoter −147 CYP4503A5 polymorphism described in Example 2 with survival rate of breast cancer patients receiving treatment with the chemotherapy drugs CY, cisplatin and BCNU.

The genomic DNA described above in Example 2 was genotyped for the Promoter −147 CYP4503A5 single nucleotide polymorphisms (SNPs) in the CYP3A5 gene. TAQMAN® assays were performed using DNA samples from each individual to identify the presence or absence of the Promoter −147 CYP4503A5 variant The primers described in Table 7 were used:

TABLE 7

PCR Primers

| PCR Primer | SEQ ID NO: | Primer Sequence |
|---|---|---|
| 3A5-147 forward | 21 | GGTGTGTGCGATTCTTTGC |
| 3A5-147 reverse | 22 | CCCTGCACAGCAGTCTTAGG |

PCR amplification was performed using 1× Perkin-Elmer TAQMAN® Reagent Mix #43C444 7 with about 900 nM 3A5-147 for primer, about 900 nM 3A5-147 rev primer, about 150 nM FAM™-labeled probe having the nucleic acid sequence 5'-CTGCAGCCCCACCTCCTTCTCC-3' (SEQ ID NO:23) and 250 nM variant VIC®-labeled probe having the nucleic acid sequence 5'-CTGCAGCCCCGCCTCCTTCTC-3' (SEQ ID NO:24). Thermal cycling was performed with at initial temperature of 50° C. for 2 min for activation of the AMPERASE® UNG in the TAQMAN® Reagent Mix followed by a denaturation step at 95° C. for 10 min, followed by 40 cycles of denaturation at 60° C. for 30 sec, primer annealing and extension was performed at 60° C. for 30 sec. The fluorescence resulting from the release of probe labels during PCR and probe hybridization was measured using a fluorometer and the ratio of FAM™-to VIC® fluorescence was calculated to determine the occurrence of the polymorphic site and homo- or heterozygosity compared to sequenced controls.

The results correlating survival with treatment are shown below in Table 8. Patients carrying the variant for CYP3A5 demonstrated significantly higher blood concentrations of CY on day 2 blood concentrations of CY were increased (p=0.0281). These patients also showed increased blood concentrations of BCNU (p=0.0479). Median survival for patients carrying the CYP3A5 SNP was about 1.3 years compared to about 2.9 years for patients without the variant.

TABLE 8

CYP4503A5 Variants and Survival. The A allele is wildtype and the B allele is mutant.

| Survival >3 years | AA | AB or BB | Total |
|---|---|---|---|
| No | 35(51.8%) | 12(85.7%) | 47 |
| Yes | 32(48.2%) | 2(14.3%) | 34 |
| Total | 67 | 14 | 81 |

| Mutation Carrier | Median Survival Rate (Years) | 95% Confidence Interval (Years) | |
|---|---|---|---|
| | | Upper Bound | Lower Bound |
| No | 2.91 | 2.28 | 4.42 |
| Yes | 1.33 | 0.75 | 2.76 |
| p-value | 0.0261 | | |

The results indicate that persons who are homozygous for the A allele have a 48.2% survival beyond 3 years compared to a 14.3% survival rate for those women who have the B allele. Blood concentrations of CY were significantly higher in patients with the B alleles and subsequently these patients showed less than ⅓ chance of survival when treated with CY than patients that are homozygous for the A allele. The data suggests that the Promoter −147 variation is detrimental to successful treatment with CY and patients with tumors for which CY treatment is typically used can be genotyped, i.e. screened, as candidates for treatment with CY. Those patients with the B allele, either AB or BB genotypes, will be less likely to benefit from treatment with CY and should be either given more of the drug, or an alternative chemotherapeutic agent with or without CY.

EXAMPLE 4

This example describes the association of the null GSTM1 polymorphism with survival rate of breast cancer patients receiving treatment with the chemotherapy drugs cyclophosphamide, cisplatin and BCNU The genomic DNA described above in Example 2 was genotyped for the null mutation of the GSTM1 gene described in detail in Abdel-Rahman et al., Cancer Letters, vol. 107, pages 229–233, 1996. Fluorescent PCR assays were performed using DNA samples from each individual to identify the presence or absence of the GSTM1 null variant. The primers described in Table 9 were used:

TABLE 9

PCR Primers

| PCR Primer | SEQ ID NO: | Primer Sequence |
|---|---|---|
| GSTM1-null forward | 27 | GAACTCCCTGAAAAGCTAAAGC |
| GSTM1-control forward | 28 | GAACTGCCACTTCAGCTGTCT |
| GSTM1-null reverse | 25 | GTTGGGCTCAAATATACGGTGG |
| GSTM1-control reverse | 26 | CAGCTGCATTTGGAAGTGCTC |

PCR amplification was performed at a MgCl$_2$ concentration of 2.5 mM in 1× buffer D (33.5 mM Tris-HCl, pH 8, 8.3 mM (NH$_4$)$_2$SO$_4$, 25 mM KCl and 0.085 mg/ml BSA) with 1.25 mM dNTPs, and 0.05 U/μl Perkin Elmer AMPLITAQ® Gold polymerase. The following primers were used in the PCR reaction: about 300 nM TET™-labeled GSTM1-null for primer, about 300 nM unlabeled GSTM1-null rev primer, about 300 nM HEX™-labeled GSTM1-control for primer and about 300 nM unlabeled GSTM1-control rev primer. Thermal cycling was performed with an initial denaturation step at 94° C. for 5 min, followed by 35 cycles of denaturation at 94° C. for 2 min, primer annealing at 59° C. for 1 min and extension at 72° C. for 1 min, followed by 10 min at 72° C. The resulting PCR products were resolved using standard acrylamide gel electrophoresis methods. The flourescence emitted from the GSTM1 PCR products and the control PCR products were compared using ABI PRISM® GENESCAN® 2.1 software (available from ABI).

The results correlating survival with treatment are shown below in Table 10. Patients homozygous for the GSTM1 null mutation had lower blood concentrations of BCNU (p=0.0240). These patients also showed improved tumor response with 58% showing complete response to therapy while only 42% of patients with both copies of the gene showed complete response (p=0.043). Median survival for patients with both GSTM1 deletions was 3.8 years compared to 1.8 years for patients with one or both GSTM1 copies.

TABLE 10

GSTM1 null mutation and Survival. Positive (+) indicates at least one copy of GSTM1, negative (−) indicates both copies are deleted.

| Survival >3 years | 0 | — | Total |
|---|---|---|---|
| No | 32(70.3%) | 16(44.4%) | 48 |
| Yes | 13(29.7%) | 20(55.6%) | 33 |
| Total | 45 | 36 | 81 |

| At Least one GSTM1 gene | Median Survival Rate (Years) | 95% Confidence Interval (years) | |
|---|---|---|---|
| | | Lower Bound | Upper Bound |
| No | 3.84 | 2.43 | — |
| Yes | 1.81 | 1.43 | 2.87 |
| p-value | 0.0109 | | |

The results indicate that persons who are missing both copies of GTSM1 have a 55.6% rate of survival beyond 3 years compared to a 29.7% survival rate for those women who have one or both copies of GSTM1. The patients missing both copies of GTSM1 had lower blood concentrations of BCNU and subsequently had a 2-fold increased chance of survival when treated with BCNU than patients with one of both copies of GSTM1. Patients with tumors for which BCNU treatment is typically used, can be genotyped, i.e. screened, as candidates for treatment with BCNU. These data suggest that absence of the GTSM1 genes may be beneficial in effective treatment with BCNU.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of screening an individual for predisposition for reduced metabolism of a CYP3A4 substrate, said method comprising:

determining the presence or absence in the individual of a G at position −392 of the promoter of a CYP3A4 gene with respect to the start codon of said CYP3A4 gene; and identifying the individual as having a predisposition for reduced metabolism of the CYP3A4 substrate if the G at position −392 of the promoter of the CYP3A4 gene wit respect to the start codon of the CYP3A4 gene is determined to be present in the individual.

2. The method of claim 1, wherein said determining comprises determining whether said individual is homozygous or heterozygous for the G at position −392 of the promoter of the CYP3A4 gene with respect to the start codon of the CYP3A4 gene.

3. The method of claim 1, wherein the CYP3A4 substrate is a nitrogen mustard or BCNU.

4. A method for selecting a treatment for a cancer patient, said method comprising:

determining the presence or absence in the cancer patient of one or both of a G at position −392 of the promoter of a CYP3A4 gene with respect to the start codon of the CYP3A4 gene and a GSTM1 null mutation; and selecting a treatment for said cancer patient selected from the group consisting of:

a treatment that does not comprise administration of an anti-cancer prodrug metabolized to the active drug by CYP3A4 if the G at position −392 of the promoter of the CYP3A4 gene with respect to the start codon of the CYP3A4 gene is determined to be present in the cancer patient;

a treatment that comprises administration of an anti-cancer prodrug metabolized to the active drug by CYP3A4 if the G at position −392 of the promoter of the CYP3A4 gene with respect to the start codon of the CYP3A4 gene is determined to be absent in the cancer patient;

a treatment that does not comprise administration of an anticancer drug which is an alkylating agent metabolized by GSTM1 if the GSTM1 null mutation is determined to be absent in the cancer patient; and a treatment that comprises administration of an anti-cancer drug which is an alkylating agent metabolized by GSTM1 if the GSTM1 null mutation is determined to be present in the cancer patient.

5. The method of claim 4, wherein said determining comprises, determining whether the cancer patient is homozygous or heterozygous for one or both of the G at position −392 of the promoter of the CYP3A4 gene with respect to the start codon of the CYP3A4 gene and the GSTM1 null mutation.

6. The method of claim 1, wherein the determining comprises:

obtaining a genomic DNA sample from the individual; and performing a PCR amplification reaction on the sample using primer pair SEQ ID:17 and SEQ ID NO:18.

7. The method of claim 3, wherein the CYP3A4 substrate is the nitrogen mustard.

8. The method of claim 7, wherein the nitrogen mustard is cyclophosphamide.

9. The method of claim 3, wherein the CYP3A4 substrate is BCNU.

10. The method of claim 4, wherein the anti-cancer prodrug is a nitrogen mustard.

11. The method of claim 10, wherein the nitrogen mustard is cyclophosphamide.

12. The method claim of 4, wherein the alkylating agent is a nitrosourea, a nitrogen mustard or cisplatin.

13. The method claim of 12, wherein the nitrosourea is BCNU.

14. The method of claim 4, wherein determining the presence or absence in the cancer patient of a G position −392 of the promoter of a CYP3A4 gene with respect to the start codon of the CPY3A4 gene comprises;

obtaining a genomic DNA sample from the cancer patient; and performing a PCR amplification reaction on the sample using primer pair SEQ ID NO:17 and SEQ ID NO:18.

15. The method of claim 4, the method comprising determining the presence or absence in the cancer patient of each of the G at position −392 of the promoter of a CYP3A4 gene with respect to the start codon of the CYP3A4 gene and the GSTM1 null mutations.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Homo sapiens

<400> SEQUENCE: 1
gacaagggca ggacagag                                               18

<210> SEQ ID NO 2
<211> LENGTH: 34
<212> TYPE: DNA
<213> ORGANISM: Homo sapiens

<400> SEQUENCE: 2
cgattctttg ctactggctg cagctgcagc cccg                             34

<210> SEQ ID NO 3
<211> LENGTH: 1345
<212> TYPE: DNA
<213> ORGANISM: Homo sapiens

<400> SEQUENCE: 3

```
ctgcagtgac cactgcccca tcattgctgg ctgaggtggt tggggtccat ctggctatct      60
gggcagctgt tctcttctct cctttctctc ctgtttccag acatgcagta tttccagaga     120
gaagggccca ctctttggca agaacctgt ctaacttgct atctatggca ggacctttga     180
agggttcaca ggaagcagca caaattgata ctattccacc aagccatcag ctccatctca     240
tccatgccct gtctctcctt taggggtccc cttgccaaca gaatcacaga ggaccagcct     300
gaaagtgcag agacagcagc tgaggcacag ccaagagctc tggctgtatt aatgacctaa     360
gaagtcacca gaaagtcaga aggatgcata gcagaggccc agcaatctca gctaagtcaa     420
ctccaccagc ctttctagtt gcccactgtg tgtacagcac cctggtaggg accagagcca     480
tgacagggaa taagactaga ctatgccctt gaggagctca cctctgttca gggaaacagg     540
cgtggaaaca caatggtggt aaagaggaaa aggacaata ggattgcatg aagggatgg      600
aaagtgccca ggggaggaaa tggttacatc tgtgtgagga gtttggtgag gaaagactct     660
aagagaaggc tctgtctgtc tgggtttgga aggatgtgta ggagtcttct aggggcaca     720
ggcacactcc aggcataggt aaagatctgt aggtgtggct tgttgggatg aatttcaagt     780
attttggaat gaggacagcc atagagacaa gggcargaga gaggcgatt aatagatttt     840
atgccaatgg ctccacttga gttctgata agaacccaga acccttggac tccccagtaa     900
cattgattga gttgtttatg atacctcata gaatatgaac tcaaaggagg tcagtgagtg     960
gtgtgtgtgt gattctttgc caacttccaa ggtggagaag cctcttccaa ctgcaggcag    1020
agcacaggtg gccctgctac tggctgcagc tccagccctg cctccttctc tagcatataa    1080
acaatccaac agcctcactg aatcactgct gtgcagggca ggaaagctcc atgcacatag    1140
cccagcaaag agcaacacag agctgaaagg aagactcaga ggagagagat aagtaaggaa    1200
agtagtgatg gctctcatcc cagacttggc catggaaacc tggcttctcc tggctgtcag    1260
cctggtgctc ctctatctgt gagtaactgt tcaggctcct cttctctgtt tcttggactt    1320
ggggtcgtaa tcaggcctct ctttt                                           1345
```

<210> SEQ ID NO 4
<211> LENGTH: 1254
<212> TYPE: DNA
<213> ORGANISM: Homo sapiens

<400> SEQUENCE: 4

```
ggcacacaaa gagacattgc atgttctcac ttatttgtgg gatctacaaa tcaaaacaat      60
tgagctaatg tctgggtctt agtcaattt gtacctaag tacagggagc acagccatta     120
gaatacatga tgaatgcttt aatacaggaa tgaataggtg agaggcacag ggtggttggg     180
tgttcttctg atacatagta tcttccttga cacattcagt acaactctca acaggtaagt     240
ctcttcatgt atgttaccct ctgaggaatt aagtggcaga acatgccttc tattatttc      300
ctttgcagaa caagaccaat tgcattagtt gggaaacagt gctggctgca tctgagcccc     360
aagcaaccat tagtctattg ctatcaccac agactcagag gggatgacac acaggggccc     420
agcaatctca cccaagtcaa ctccaccaac atttctggtc acccaccatg tgtacagtac     480
cctgctaggg tccagggtca tgaaagtaaa aataccaga ctgtgcccctt gaggaactca    540
cctctgctaa gggaaacagg cacagaaacc cacaagggtg gtagagagga ataggacaa      600
taggactgtg tgagggggat aggaggcacc cagaggagga aatggttaca tctgtgtgag     660
```

-continued

```
gaggttggta aggaaagact ttaatagaag gggtctgtct ggctgggctt gcaaggatgt     720
gtaggagtca tctaggggc  acaagtacac tccaggcaga gggaattgca tgggtaaaga     780
tctgcagttg tggcttgtgg ggatggattt caagtattct ggaatgaaga cagccatgga    840
aacaagggca ggtgagagga tatttaagag gcttcatgcc aatggctcca cttcagtttc    900
tgataagaac tcaggttccg tggactccct gataaaactg attaagttgt ttatgattcc    960
ccatagaata tgaactcaaa ggaggtaagc aaagggtgt  gtgcgattct ttgctactgg   1020
ctgcagctgc agccccacct ccttctccag cacataaaca tttcagcagc ttgacctaag   1080
actgctgtgc agggcaggga tgctccaggc agacagccca gcaaacaaca gcacacagct   1140
gaaagtaaga ctcagaggag acagttgaag aaggcaagtg gcgatggacc tcatcccaaa   1200
tttggcggtg gaaacctggc ttctcctggc tgtcagcctg gtgctcctct atct         1254
```

<210> SEQ ID NO 5
<211> LENGTH: 18
<212> TYPE: DNA
<213> ORGANISM: Homo sapiens

<400> SEQUENCE: 5

```
gacaagggca agagagag                                                   18
```

<210> SEQ ID NO 6
<211> LENGTH: 34
<212> TYPE: DNA
<213> ORGANISM: Homo sapiens

<400> SEQUENCE: 6

```
cgattctttg ctactggctg cagctgcagc ccca                                 34
```